(12) United States Patent
Lee (10) Patent No.: US 6,591,141 B2
(45) Date of Patent: Jul. 8, 2003

(54) MAT FOR HOT COMPRESS AND ACUPRESSURE MOUNTED WITH NEW TYPE HYPERTHERMO-RADIATIVE APPARATUS

(75) Inventor: Hwan Sung Lee, Seoul (KR)

(73) Assignee: Ceragem International, Inc., Los Angeles, CA (US)

( * ) Notice: Subject to any disclaimer, the term of this patent is extended or adjusted under 35 U.S.C. 154(b) by 9 days.

(21) Appl. No.: 09/990,861

(22) Filed: Nov. 13, 2001

(65) Prior Publication Data

US 2002/0058973 A1 May 16, 2002

(30) Foreign Application Priority Data

| Nov. 15, 2000 | (KR) | 2000-67867 |
| Nov. 23, 2000 | (KR) | 2000-32892 |
| Nov. 25, 2000 | (KR) | 2000-33080 |
| Dec. 4, 2000 | (KR) | 2000-73144 |

(51) Int. Cl.[7] ................................................. A61F 7/12
(52) U.S. Cl. ............................. 607/98; 607/96; 601/19; 601/20
(58) Field of Search ...................... 607/90, 91, 96–102, 607/154, 156; 606/201, 204, 237–245; 601/19, 20

(56) References Cited

U.S. PATENT DOCUMENTS 3,645,256 A * 2/1972 Morrison
5,094,225 A * 3/1992 Craw

FOREIGN PATENT DOCUMENTS

JP 58-073237 5/1983 .......... A61H/15/00

* cited by examiner

*Primary Examiner*—Roy D. Gibson
(74) *Attorney, Agent, or Firm*—Lee & Hong

(57) ABSTRACT

The present invention, which relates to a mat for hot compress and acupressure equipped with a roller type hyperthermo-radiative apparatus, is designed to minimize friction resistance upon horizontal movement thereof. The mat includes a mat member foldable at one side thereof and with a longitudinal groove formed in the center thereof. Curved rails are formed at both sides of the central groove on the bottom of the mat member, which has curved portions corresponding to the curvature of the vertebral region of a user. Also, a roller type hyperthermo-radiative apparatus that travels along the curved rails and a conveying mechanism for moving the roller type hyperthermo-radiative apparatus in a horizontal direction are included. Finally, there is a control panel for controlling the conveying mechanism and an operating unit for adjusting a position of the roller type hyperthermo-radiative apparatus.

22 Claims, 12 Drawing Sheets

MAT FOR HOT COMPRESS AND ACUPRESSURE MOUNTED WITH NEW TYPE HYPERTHERMO-RADIATIVE APPARATUS

BACKGROUND OF THE INVENTION

1. Field of the Invention

The present invention relates to a mat for hot compress and acupressure mounted with a new type hyperthermo-radiative apparatus, and more particularly, a mat for hot compress and acupressure mounted with a roller type hyperthermo-radiative apparatus designed to minimize friction resistance of the apparatus upon horizontal movement thereof.

2. Description of the Prior Art

The present invention relates to improvements on the invention disclosed in Korean Patent Application No. 1999-26985 entitled "a treatment mat" (which was filed on Jan. 14, 2000 in U.S.A. and issued U.S. Pat. No. 6,243,609 on Jun. 5, 2001).

Figure 1A:
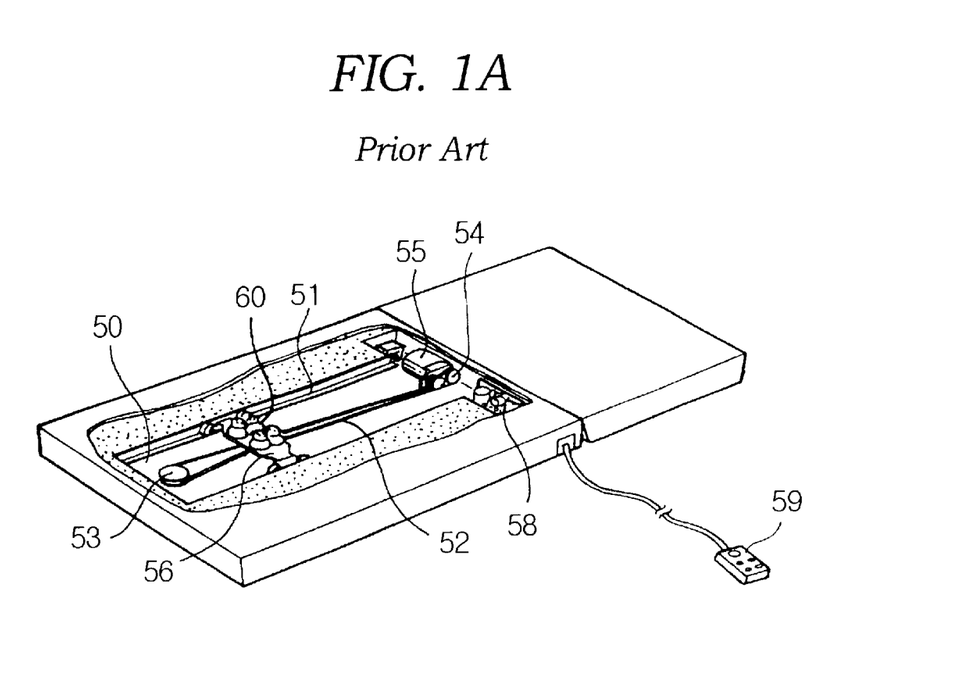
FIGS. 1A and 1B show a conventional mat for hot compress and acupressure and a conventional hyperthermo-radiative apparatus, respectively.
Figure 1B:
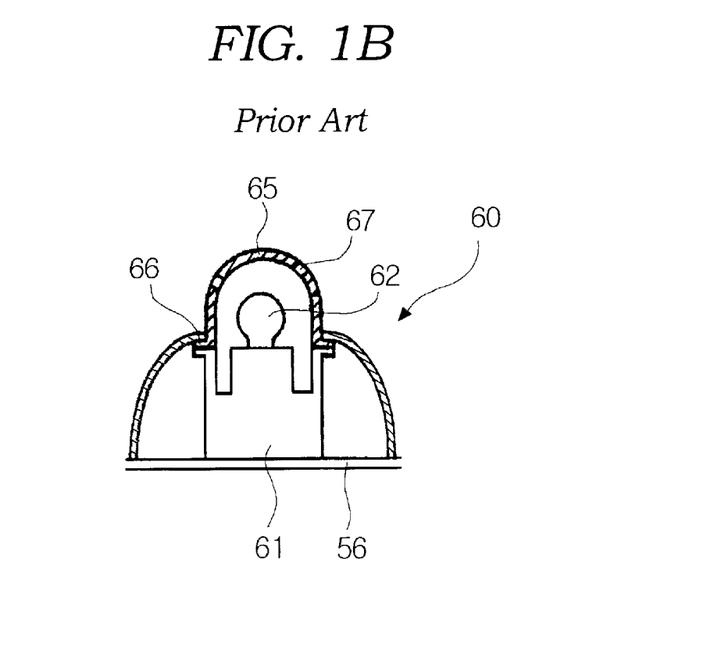

FIG. 1A shows the conventional mat for hot compress and acupressure, and FIG. 1B shows a sectional view of the conventional hyperthermo-radiative apparatus. As shown well in FIG. 1A, the conventional mat for hot compress and acupressure comprises a backing plate 50 formed on a lower side corresponding to a longitudinal groove at the center thereof, rails 51 installed on the left and right sides of the backing plate 50, a hyperthermo-radiative apparatus 60 moving horizontally along the rails 51, a horizontal moving means for causing the hyperthermo-radiative apparatus 60 to move horizontally, a control panel 58 for controlling the horizontal moving means, and an operating unit 59 for controlling the position of the hyperthermo-radiative apparatus 60. Further, the horizontal moving means includes a motor 55 installed on one side of the mat for hot compress and acupressure, a pulley 54 connected directly with the motor 55, and a rope 52 for transmitting driving force from the motor 55 to the hyperthermo-radiative apparatus 60 through the pulley 54. Here, the mat for hot compress and acupressure is covered with a mat cloth (not shown) that can sufficiently cover the longitudinal groove located at the center of the mat. Thus, the external appearance of the mat can be protected and the hyperthermo-radiative apparatus 60 can be prevented from coming into direct contact with a vertebral region of a user.

Furthermore, the conventional hyperthermo-radiative apparatus 60 that has been used in the mat for hot compress and acupressure is schematically shown in FIG. 1B. That is, the conventional hyperthermo-radiative apparatus 60 comprises a supporting stand 61 fixed to a supporting plate 56 for supporting the entire portion of the apparatus, a lamp 62 installed on the supporting stand 61, and a cap 65 for transferring heat generated from the lamp 62 and protecting the lamp 62. Here, the cap 65 is constructed in such a manner that an upper portion thereof is hemispherical, a central portion thereof is hollow cylindrical, and a lower portion thereof is provided with an outwardly flared flange 66. The upper portion of the cap is formed with a plurality of small holes 67 to emit the heat.

Therefore, when a user who wishes to obtain the effects of the hot compress and acupressure intends to utilize the conventional mat for hot compress and acupressure constructed as such, the user first lies down on the mat and presses down a button on the operating unit 59. Then, the motor 55 is actuated during a time when the button continues to be pressed down. Thereafter, the hyperthermo-radiative apparatus 60 is pulled through the pulleys 53, 54 and the rope 52, and is conveyed horizontally on the rails 51 in a longitudinal direction. When the hyperthermo-radiative apparatus 60 is completely moved to one side of the rails 51, a reverse switch (not shown) installed on a distal end of the rails 51 causes the flow direction of current applied to the motor 55 to be changed in the opposite flow direction. Thus, the hyperthermo-radiative apparatus 60 comes to stop temporarily, changes its direction of movement, and then moves again in the opposite direction. That is, at least while the user presses down the button on the operating unit 59, the hyperthermo-radiative apparatus 60 advances completely in one direction and then in the opposite direction again. During the horizontal movement, the hyperthermo-radiative apparatus 60 emits the heat from the lamp 62 installed therein, and the heat reaches the vertebral region of the user through the small holes 67. Consequently, a hot compress effect can be obtained. At the same time, while the hemispherical cap 65 located at an uppermost end of the hyperthermo-radiative apparatus 60 moves along the rails 51 in a straight line, the vertebral region of the user lying down on the mat is caused to get acupressure in the straight line.

However, in case of the conventional mat for hot compress and acupressure, while the hyperthermo-radiative apparatus 60 is moved, the cap 65 should be moved in a state where it is pressed down by the vertebral region of the user lying down on the mat for hot compress and acupressure. Thus, friction force is generated in the mat cloth (not shown) positioned between the user and the hyperthermo-radiative apparatus, and causes the protective cloth to be easily damaged. In addition, the user feels a pain on his/her vertebral region due to the friction force. Further, it was difficult to manufacture the conventional hyperthermo-radiative apparatus 60 since the protective cap 65 thereof should be machined in the form of the hemisphere. The difficulty in manufacturing the apparatus was aggravated since the cap was made thinner in order to accomplish more rapid heat transfer.

Furthermore, the conventional mat for hot compress and acupressure has required more power in moving the hyperthermo-radiative apparatus 60 due to friction resistance between the user and the hyperthermo-radiative apparatus 60. Consequently, the large motor for generating high driving force was used, and thus, consumption of unnecessary electric power was incurred. In addition, when the hyperthermo-radiative apparatus 60 is moved in the conventional mat for hot compress and acupressure, excessive load is produced due to the friction resistance. If the load cannot be overcome, the rope 52 slips onto the pulley 53. Thus, there was a problem in that the hyperthermo-radiative apparatus 60 cannot be normally moved.

Moreover, since the rails 51 are installed in the form of the straight line within the conventional mat for hot compress and acupressure, the hyperthermo-radiative apparatus 60 cannot come into smooth contact with curved portions near the nape of the neck and vertebrae of the user. Thus, the effects thereof cannot be fully obtained. In addition, since the hyperthermo-radiative apparatus 60 performs the hot compress treatment only for the vertebral region where the apparatus 60 passes, the other portion except the vertebral region cannot be subjected to the far infrared treatment. Thus, there was a disadvantage in that overall effects thereof were lowered.

SUMMARY OF THE INVENTION

Therefore, the present invention is conceived to solve the aforementioned problems in the prior art and is directed to a mat for hot compress and acupressure mounted essentially with a new type hyperthermo-radiative apparatus for use in hyperthermo-radiatitive effect.

An object of the present invention is to provide a mat for hot compress and acupressure wherein a roller type hyperthermo-radiative apparatus, which can minimize friction force generated when the apparatus moves horizontally within a central portion of the mat for hot compress and acupressure, is essentially employed.

Another object of the present invention is to provide a mat for hot compress and acupressure wherein the effects of the hot compress and acupressure imposed on a user can be enhanced by employing a roller type hyperthermo-radiative apparatus and simultaneously forming curved portions onto conveying rails corresponding to curved regions of the user.

A further object of the present invention is to provide a mat for hot compress and acupressure wherein more efficient effects of the hot compress and acupressure on a user can be obtained by employing a roller type hyperthermo-radiative apparatus and simultaneously improving a conveying means for moving the hyperthermo-radiative apparatus.

A still further object of the present invention is to provide a mat for hot compress and acupressure wherein the effects of the hot compress and acupressure on a user can be further enhanced by employing a roller type hyperthermo-radiative apparatus and simultaneously utilizing an additional far infrared heating means for transferring the far infrared radiation to a user's region to be treated regardless of moving positions of the apparatus.

According to an aspect of the present invention for achieving the objects, there is provided a mat for hot compress and acupressure, comprising a mat member foldable at one side thereof and with a longitudinal groove formed in the center thereof, curved rails formed at both sides of the central groove on the bottom of the mat member and with curved portions corresponding to the curvature of the vertebral region of a user; a roller type hyperthermo-radiative apparatus traveling along the curved rails; a conveying means for moving the roller type hyperthermo-radiative apparatus in a horizontal direction; a control panel for controlling the conveying means; and an operating unit for adjusting a position of the roller type hyperthermo-radiative apparatus.

According to the present invention, it is preferred that the roller type hyperthermo-radiative apparatus includes a backing plate with wheels fixedly supported at four corners thereof; a plurality of pairs of supporting means mounted on the backing plate; roller type rotating members rotatably installed between respective pairs of the supporting means and with cylindrical empty spaces formed therein; heating members inserted into the empty spaces of the rotating members from both ends of the spaces; socket portions connected to the heating members for supplying external electric power; and bearing members for fixedly supporting the socket portions to the supporting means and for rotatably coupling the rotating members thereto.

Further, according to the present invention, the mat for hot compress and acupressure can be compactly manufactured and noise generated therefrom can also be reduced, by improving the conveying means for moving the hyperthermo-radiative apparatus.

Furthermore, according to the present invention, a hot compress effect can be exerted on lateral vertebral regions, arm regions and lower parts of the user's body since the far infrared heating means for emitting the far infrared radiation are disposed at both sides of the groove in the mat member and below the other mat member.

BRIEF DESCRIPTION OF THE DRAWINGS

The above objects and features of the present invention will become apparent from the following description of preferred embodiments given in connection with the accompanying drawings, in which:

FIGS. 4A to 4C show other preferred embodiments of the roller type hyperthermo-radiative apparatus, and in particular.

FIGS. 5A to 5C are conceptual views for schematically showing the interrelationship between the roller type hyperthermo-radiative apparatus and the curved rails, and in particular.

DETAILED DESCRIPTION OF THE INVENTION

Hereinafter, preferred embodiments of the present invention will be described in detail with reference to the accompanying drawings.

The present invention is directed to a mat for hot compress and acupressure including a roller type hyperthermo-radiative apparatus 100.

Figure 2A:
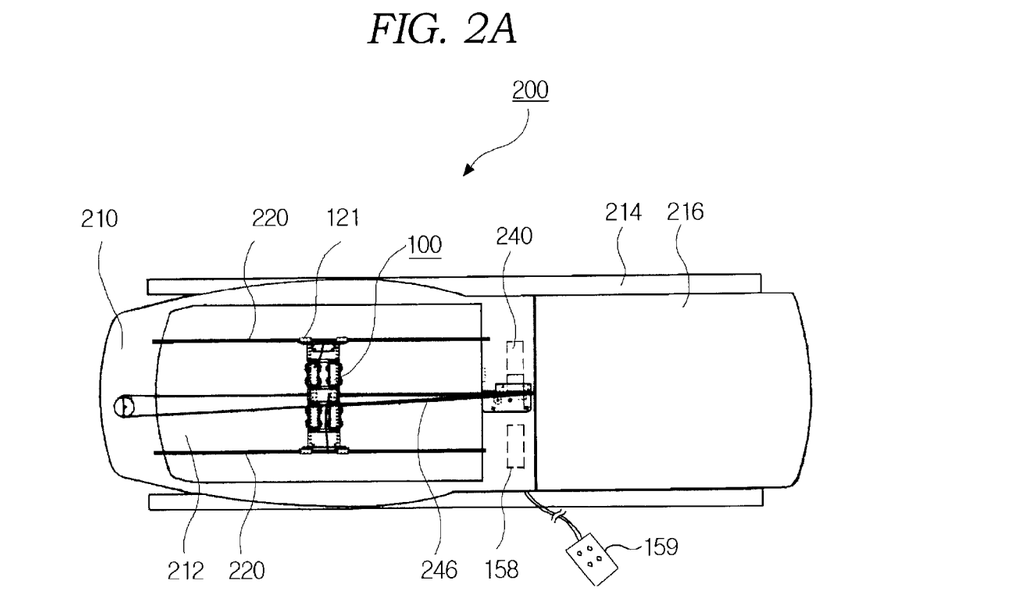
FIG. 2A is a plan view of a mat for hot compress and acupressure according to a preferred embodiment of the present invention as viewed from above.
Figure 2B:
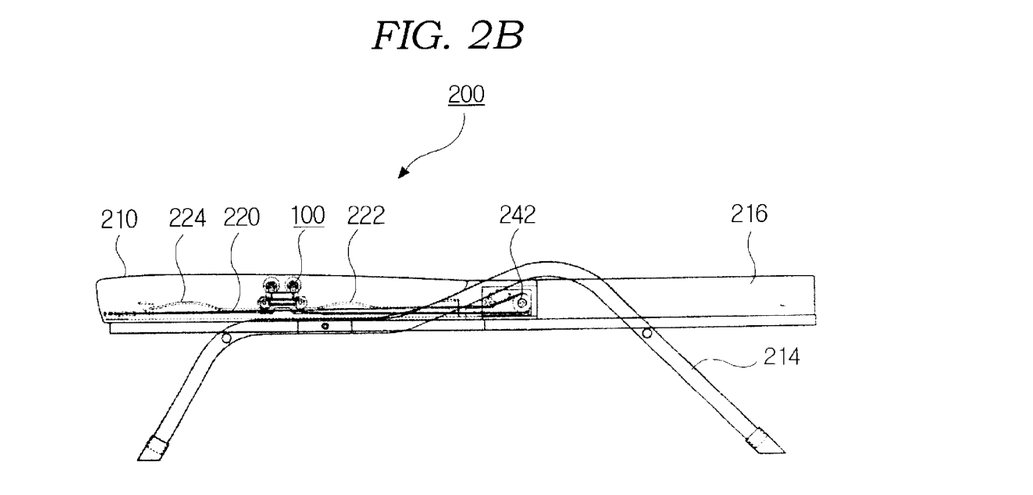
FIG. 2B is a front view of the mat for hot compress and acupressure.

FIG. 2A is a plan view of the mat for hot compress and acupressure 200 according to a preferred embodiment of the present invention as viewed from above, and FIG. 2B is a front view of the mat for hot compress and acupressure 200. The mat for hot compress and acupressure 200 of the present invention may comprise a mat member 210 with a longitudinal groove 212 formed in the center thereof, and another mat member 216 electrically connected to and foldable toward the mat member 210. The mat for hot compress and acupressure 200 of the present invention may comprise curved rails 220 formed at both sides of the central groove 212 on the bottom of the mat member 210 and with curved portions corresponding to the curvature of the vertebral region of a user. The longitudinal groove 212 formed in the center of the mat member 210 provides a space for accommodating essential components of the present invention. The mat for hot compress and acupressure 200 of the present invention may essentially comprise the roller type hyperthermo-radiative apparatus 100 traveling along the curved rails 220. The mat for hot compress and acupressure 200 of the present invention may comprise the conveying means for moving the roller type hyperthermo-radiative apparatus 100 in a horizontal direction. The mat for hot compress and acupressure 200 of the present invention may comprise a control panel 158 for controlling the conveying means and an operating unit 159 for adjusting a position of the roller type hyperthermo-radiative apparatus 100. In use, the mat members 210, 216 can be mounted onto a frame body 214 with prefabricated legs.

Figure 3A:
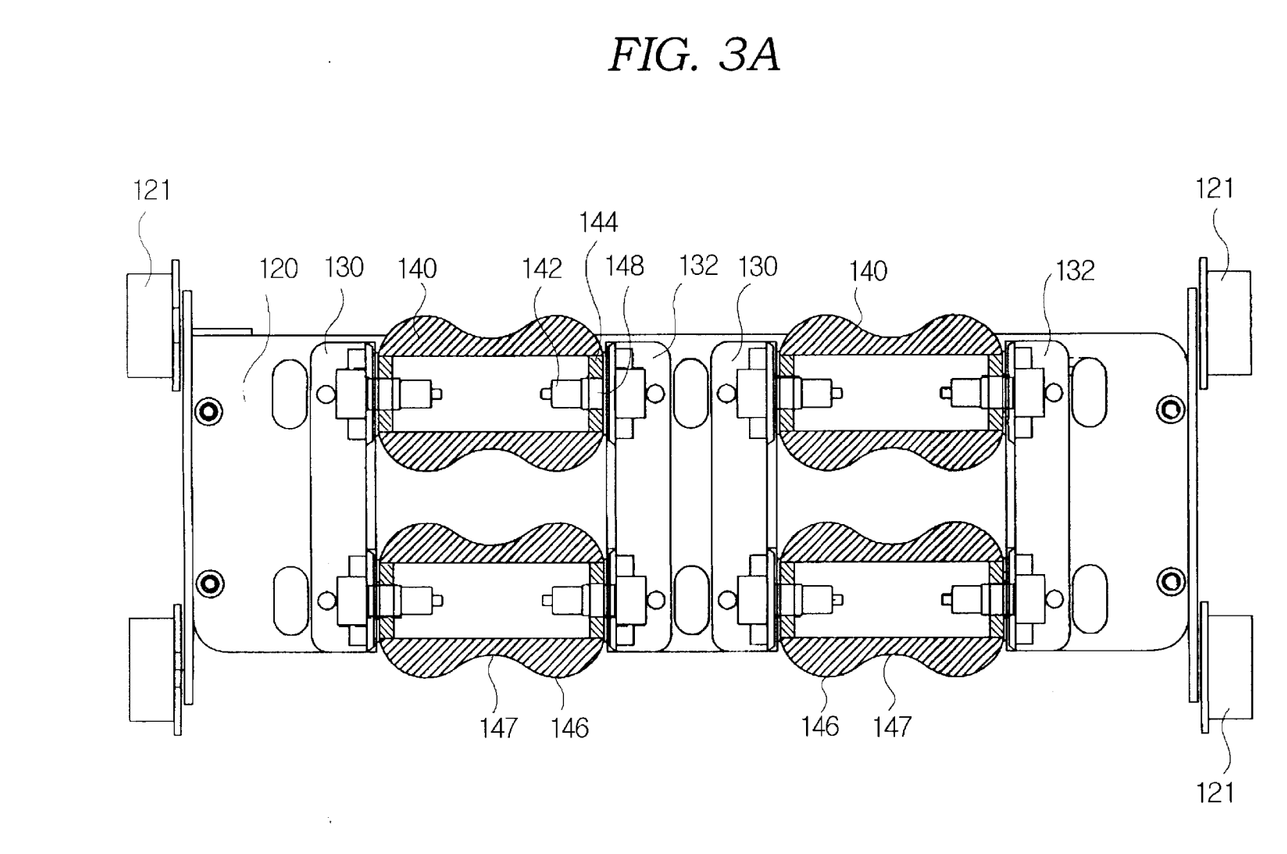
FIG. 3A is a plan view of the roller type hyperthermo-radiative apparatus, with rotating members cut away.
Figure 3B:
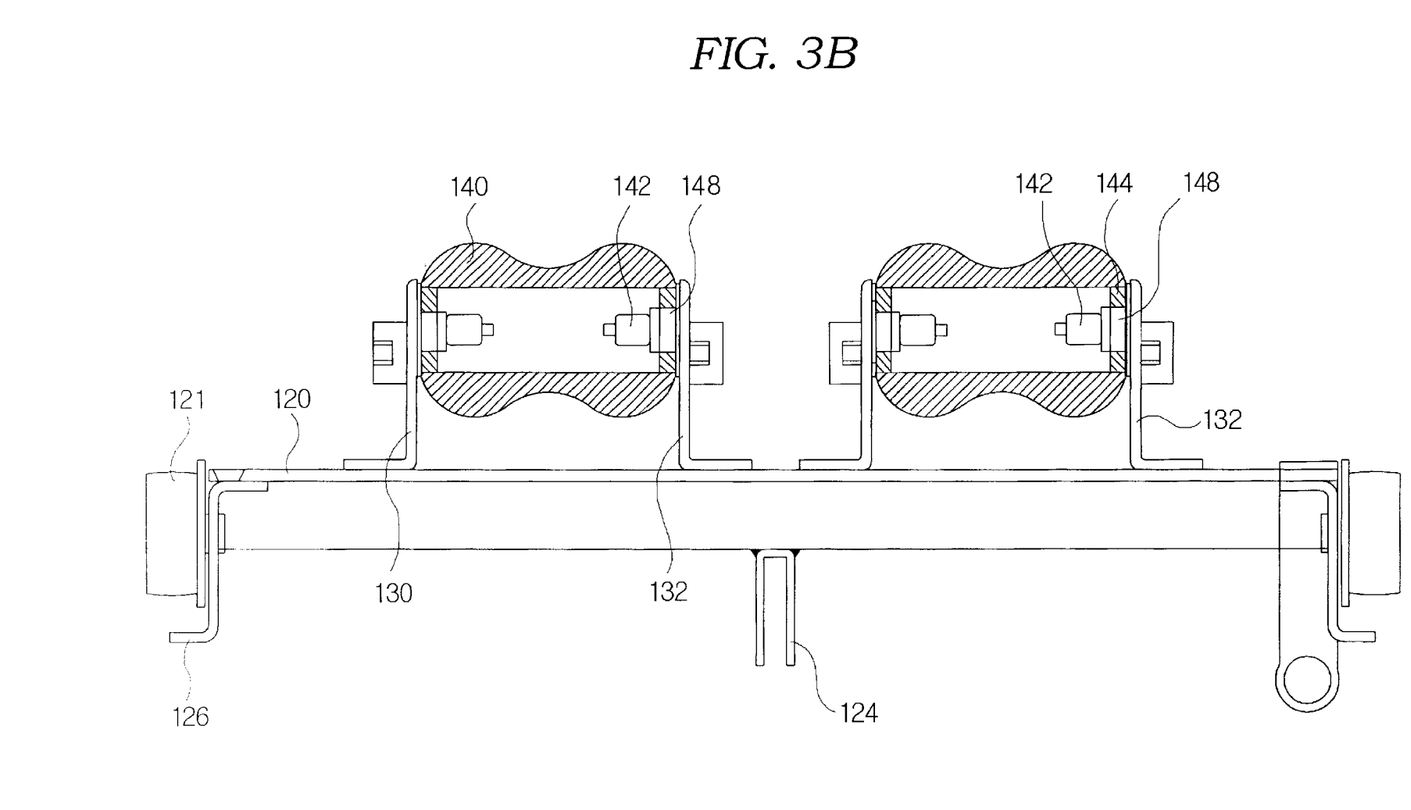
FIG. 3B is a front view of the roller type hyperthermo-radiative apparatus with the rotating members cut away.
Figure 3C:
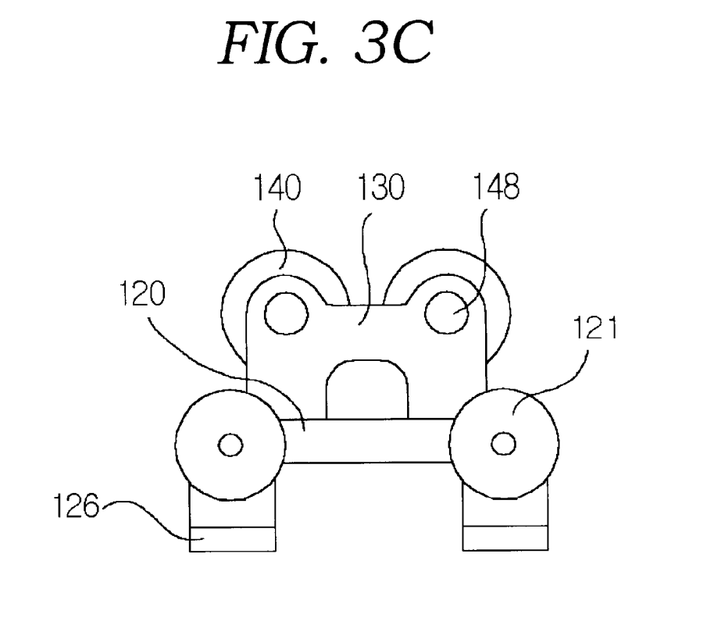
FIG. 3C is a left side view of the roller type hyperthermo-radiative apparatus.

FIG. 3A is a plan view of the roller type hyperthermo-radiative apparatus 100, as viewed from above, with rotating members cut away; FIG. 3B is a front view of the roller type hyperthermo-radiative apparatus 100, with the rotating members cut away; and FIG. 3C is a left side view of the roller type hyperthermo-radiative apparatus 100. The mat for the hot compress and acupressure 200 according to the present invention includes the roller type hyperthermo-radiative apparatus 100. The roller type hyperthermo-radiative apparatus 100 comprises a backing plate 120 with wheels 121 that move along rails 220. The backing plate 120 comprises a plurality of pairs of supporting means 130, 132 that are installed to be opposed to each other on a plane thereof. The backing plate 120 is provided with connecting members 124 for coupling the plate with the conveying means, at front and rear central portions thereof. Further, the plate 120 is provided with the wheels 121 and flanges 126 disposed below the wheels, at four corners thereof. Since the flanges 126 are fitted below the rails 220, the flanges allow the roller type hyperthermo-radiative apparatus 100 to move stably and prevent the apparatus from running off the rails 220 when the wheels 121 of the apparatus roll on the rails 220. The hyperthermo-radiative apparatus 100 includes roller type rotating members 140 between the plurality of pairs of the supporting means 130, 132. The rotating members 140 are rotatably installed between the supporting means 130, 132. A cylindrical empty space where heating members 142 inserted from both ends of the space are accommodated is formed within the interior of the rotating member 140. When the hyperthermo-radiative apparatus 100 moves while coming into contact with a body of the user, the rotating members 140 rotate on their own axes while exerting slight pressure on the body of the user. Thus, friction resistance of the rotating members can be greatly reduced, and the power needed for moving the hyperthermo-radiative apparatus 100 can also be reduced. Further, it is preferred that the rotating members 140 be made of an inorganic mineral from which the far infrared radiation can be emitted. The reason is that in order to improve the effects of the present invention, the rotating members 140 should provide the user's region to be treated with an acupressure effect and also emit the far infrared radiation thereto. In the present invention, it is preferred that the inorganic mineral be comprised of jade as a major composition. It is also preferred that the rotating members 140 be formed with external surfaces thereof being curved, in order to improve the acupressure effect on the body of the user. That is, the external surfaces may comprise peak portions 146 which protrude toward the outside, and valley portions 147 which are relatively indented. In such a case, since the peak portions 146 exert the slight pressure on the body of the user, the acupressure effect on the user can be further enhanced. On the other hand, heat is generated from the heating members 142 by an external power source. When high temperature heat is emitted, the heat is transferred to the body of the user and the far infrared radiation is also emitted from the rotating members 140. In the present invention, it is preferred that infrared lamps be used as the heating members 142. The heating members 142 are connected to socket portions 148. Preferably, the heating members 142 are not rotated unlike the roller type rotating members 140, and they are fixedly installed. To this end, it is preferred that bearing members 144 be positioned and used between the socket portions 148 and the roller type rotating members 140. The bearing members 144 may be constructed in such a manner that inner rings thereof are coupled with the socket portions 148 whereas outer rings thereof are coupled with the rotating members 140. Furthermore, the socket portions 148 also perform a function of transferring the external electric power to the heating members 142. Herein, the hyperthermo-radiative apparatus as described above and as shown in FIGS. 3A to 3C will be referred to as a "general roller type hyperthermo-radiative apparatus".

Figure 4A:
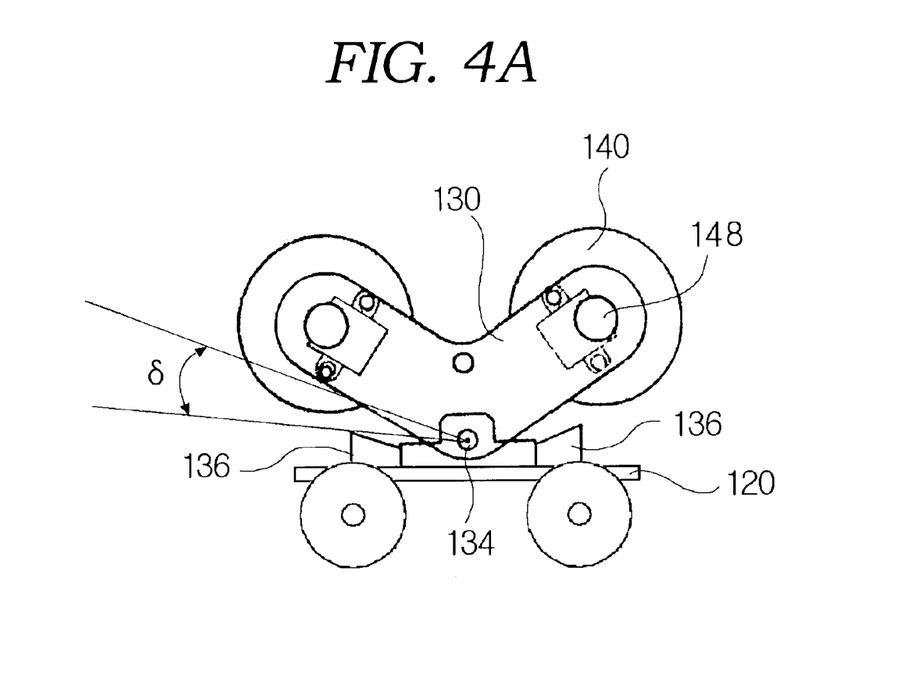
FIG. 4A shows a V-shaped roller type hyperthermo-radiative apparatus.
Figure 4B:
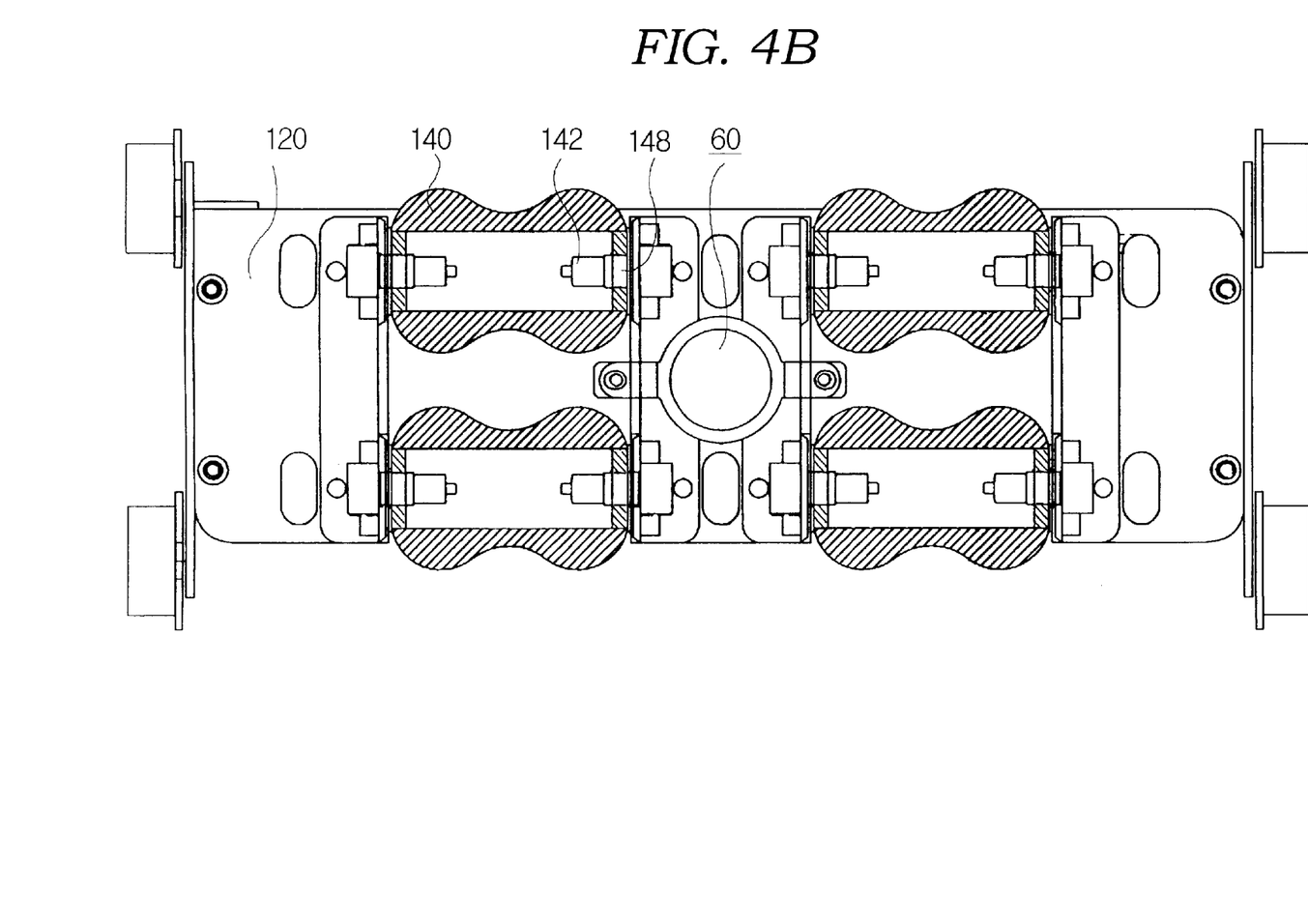
FIG. 4B shows a hybrid roller type hyperthermo-radiative apparatus.
Figure 4C:
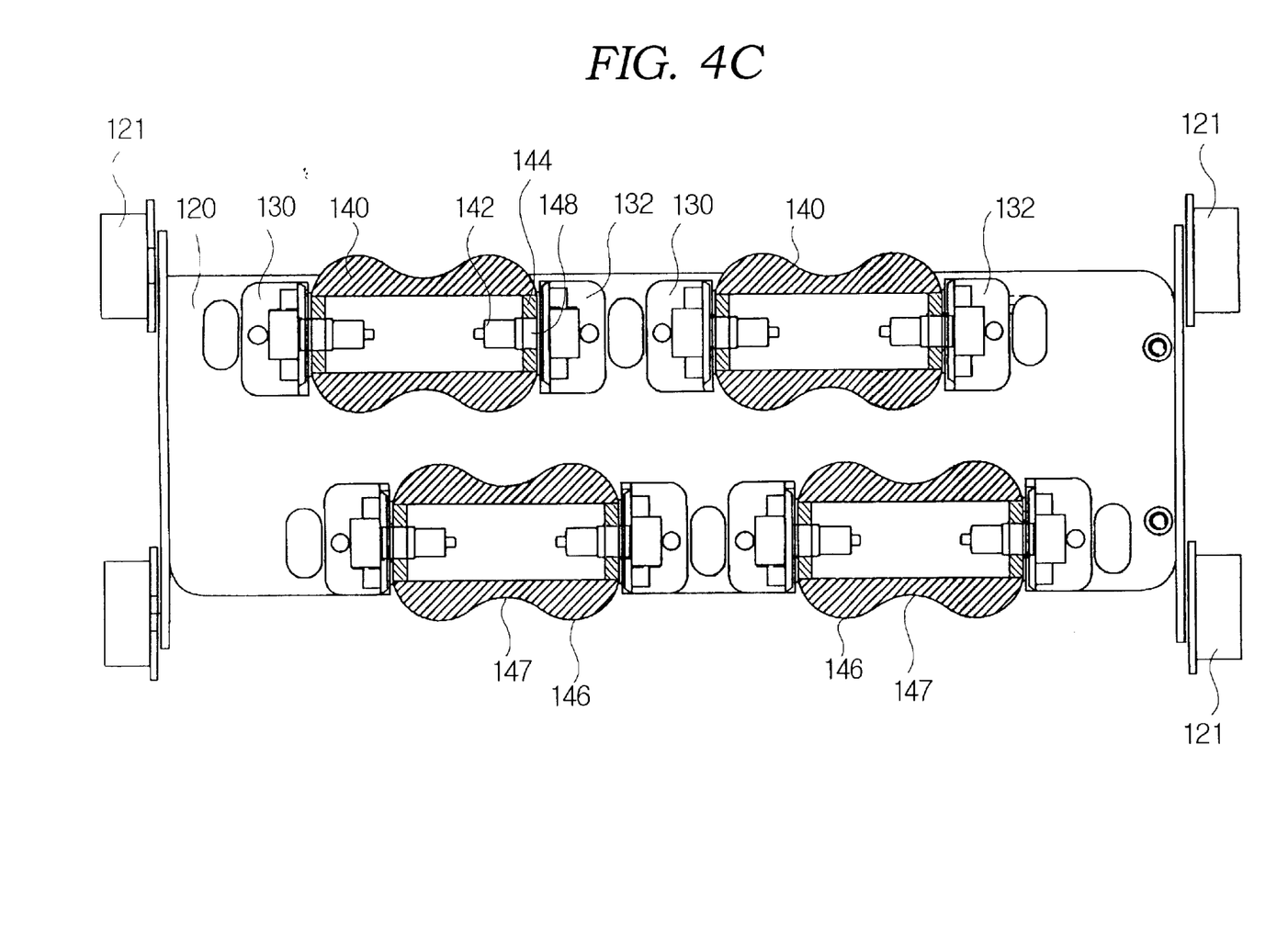
FIG. 4C shows a cross roller type hyperthermo-radiative apparatus.

FIGS. 4A to 4C show other preferred embodiments of the roller type hyperthermo-radiative apparatus 100, respectively. FIG. 4A is a side view showing one of the preferred embodiments of the roller type hyperthermo-radiative apparatus 100 wherein the supporting means 130, 132 are further improved. It is preferred that the supporting means 130, 132 be generally constructed in a V shape and a shaft 134 be formed at a lower vertex of the V-shaped supporting means 130, 132 to perform a function of hinge with respect to the backing plate 120. Further, stoppers 136 are formed on the backing plate 120 disposed below the V-shaped supporting means 130, 132, and thus, the supporting means 130, 132 can be prevented from slanting excessively toward either side. It is preferred that the stoppers 136 be made of elastic material in order to reduce impact. On the other hand, an angle formed between the V-shaped supporting means 130, 132 and the stopper 136 with respect to the shaft 134 as a vertex is δ which greatly correlates with an angle α formed between the horizontal plane and curved portions 222, 224 of the curved rails 220. Herein, the hyperthermo-radiative apparatus in which the V-shaped supporting means 130, 132 and the hinge shafts 134 are formed will be referred to as a "V-shaped roller type hyperthermo-radiative apparatus". In particular, the V-shaped roller type hyperthermo-radiative apparatus can be usefully employed in the curved rails 220 having the curved portions 222, 224.

FIG. 4B shows one of other preferred embodiments of the roller type hyperthermo-radiative apparatus 100 wherein the conventional hyperthermo-radiative apparatus 60 is further provided in an empty space between the plurality of the rotating members 140. The hyperthermo-radiative apparatus 60 has the same basic construction as shown in FIG. 1B and is fixed to the backing plate 120. Herein, the hyperthermo-radiative apparatus in which the new hyperthermo-radiative apparatus with the roller type rotating members used therein is employed together with the conventional hyperthermo-radiative apparatus will be referred to as a "hybrid roller type hyperthermo-radiative apparatus". Since the mat 200 according to the present invention comprises the hybrid roller type hyperthermo-radiative apparatus, the rotating members 140 and the conventional hyperthermo-radiative apparatus 60 of the hybrid roller type hyperthermo-radiative apparatus can emit the far infrared radiation evenly to the user's body FIG. 4C shows a further preferred embodiment of the roller type hyperthermo-radiative apparatus 100, wherein the plurality of rotating members 140 are slightly staggered with respect to one another. Here, it is sufficient that the supporting means 130, 132 are slightly staggered laterally with respect to the advancing direction of the hyperthermo-radiative apparatus, or they are manufactured in the form of "V" in which the supporting means are slightly bent laterally with respect to the advancing direction of the hyperthermo-radiative apparatus. In this case, the rotating members 140 can emit the far infrared radiation evenly to the user's body in the advancing direction thereof. Further, since the curved peak portion 146 is placed to be followed by the valley portion 147 of the next rotating member 140 in the advancing direction, the number of portions for exerting acupressure on the user increases as large as the number of the peak portions 146. Thus, more excellent acupressure effect can be obtained. In such case, there is no need for additional installation of the conventional hyperthermo-radiative apparatus 60 in the empty space between the rotating members 140, as shown in FIG. 4B. Herein, such hyperthermo-radiative apparatus in which the roller type rotating members are staggered with respect to one another will be referred to as a "cross roller type hyperthermo-radiative apparatus." In the present invention, insofar the roller type hyperthermo-radiative apparatus 100 is not specifically defined, it is intended to include all of the general roller type hyperthermo-radiative apparatus, V-shaped roller type hyperthermo-radiative apparatus, hybrid roller type hyperthermo-radiative apparatus and the cross roller type hyperthermo-radiative apparatus, which are described in detail above and illustrated in FIGS. 3A to 3C and FIGS. 4A to 4C.

Figure 5A:
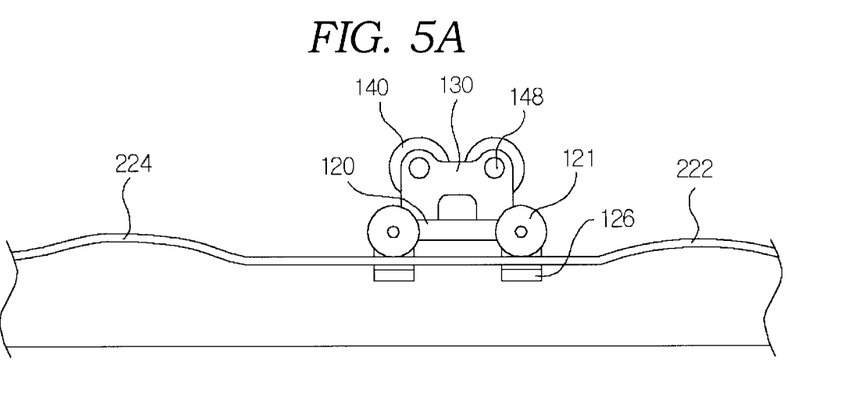
FIG. 5A shows a state where the roller type hyperthermo-radiative apparatus approaches toward curved portions of curved rails.
Figure 5B:
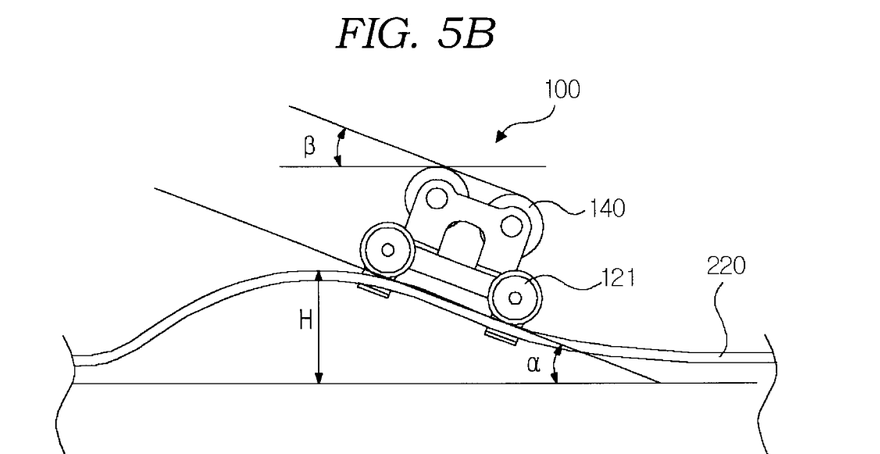
FIG. 5B shows a state where a general roller type hyperthermo-radiative apparatus approaches and ascends the curved portions of the curved rails.
Figure 5C:
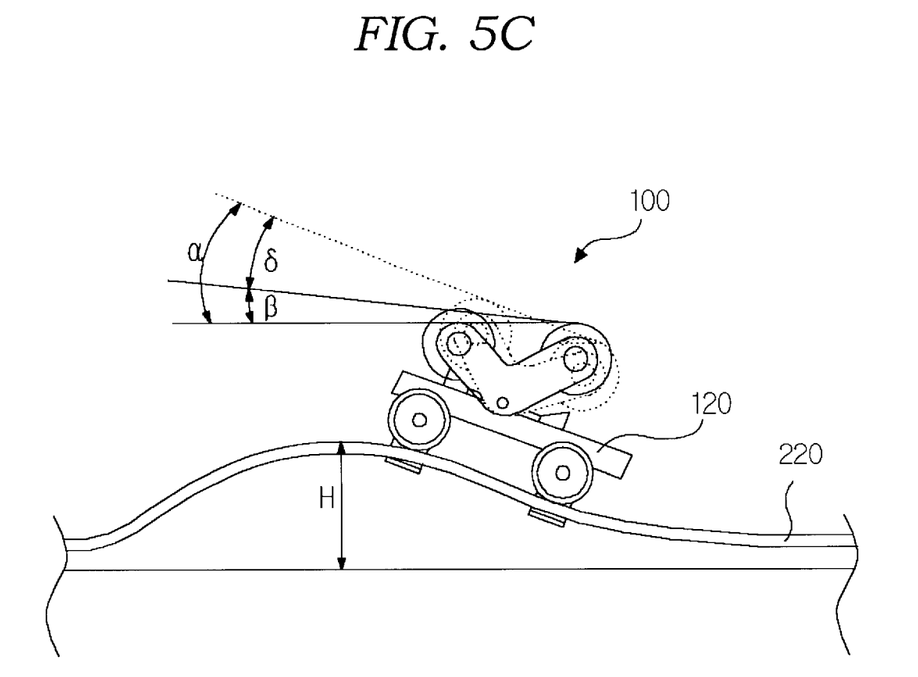
FIG. 5C shows a state where the V-shaped roller type hyperthermo-radiative apparatus approaches and ascends the curved portions of the curved rails.

FIGS. 5A to 5C are conceptual views for schematically showing the interrelationship between the roller type hyperthermo-radiative apparatus 100 and the curved rails 220. The mat for the hot compress and acupressure 200 according to the present invention includes the respective curved rails 220 at both sides of the longitudinal groove 212 on the bottom of the mat. Each curved rail 220 includes the curved portion 222 corresponding to the curvature of the lumbar vertebral region of the user, and the curved portion 224 corresponding to the nape region of the neck of the user. Since the lumbar vertebral region and the nape region of the neck of the user are not flattened but slightly curved upwardly when the user lies down on the mat, the curved portions 222, 224 are designed to uniformly exert the hot compress and acupressure even on the lumbar vertebral region and the nape region of the neck of the user by raising the roller type hyperthermo-radiative apparatus 100 at the lumbar vertebral region and the nape region of the neck of the user in accordance with the curved portions 222, 224 of the rails. At this time, it is preferred that the curved portions 222, 224 be formed to slope somewhat gently. The degree of gentle slope may have an interrelationship depending on the roller type hyperthermo-radiative apparatus 100 (see FIGS. 5A to 5C).

FIG. 5A shows a state where the roller type hyperthermo-radiative apparatus 100 approaches toward the curved portions of the curved rails. FIG. 5B shows a state where the general roller type hyperthermo-radiative apparatus approaches and ascends the curved portion 222. FIG. 5C shows a state where the V-shaped roller type hyperthermo-radiative apparatus approaches and ascends the curved portion 222. Assuming that the angle formed between the general roller type hyperthermo-radiative apparatus 100 and the horizontal plane at a position where the general roller type hyperthermo-radiative apparatus 100 ascends the curved portion is α (alpha) in FIG. 5B, the angle actually formed between the horizontal plane (the vertebral region of the user) and the two rotating members 140 becomes β (beta). At this time, as for the general roller type hyperthermo-radiative apparatus 100, the angles α and β are identical to each other. Therefore, in a case where the general roller type hyperthermo-radiative apparatus 100 is employed in the mat for the hot compress and acupressure of the present invention, as the angle α is set smaller, the pressure exerted on the vertebral region of the user who lies down on the mat is lowered. Accordingly, it is preferable to set the angle α smaller. However, if the angle α is set smaller, the height H generated by the curved portions 222, 224 is lowered. Thus, it is difficult to sufficiently obtain its acupressure effects to the necked and the vertebral region of the user. In order to overcome the conflict therebetween, there is an urgent need for a method of reducing the angle β while increasing the angle α. In order to meet the need, the V-shaped roller type hyperthermo-radiative apparatus 100 is employed as in FIG. 5C.

In FIG. 5C, when the V-shaped roller type hyperthermo-radiative apparatus 100 ascends the curved portions 222, 224, the angle formed between the horizontal plane and the backing plate 120 is α, whereas the angle formed between the horizontal plane and the two rotating members 140 is β. At this time, the angle β is always smaller than the angle α. This is because the two rotating members 140 have a tendency that they intend to be in the horizontal state by means of the hinge shaft 134 by being subjected to the same weight of the user. This tendency is naturally generated in the range of angle δ formed between the V-shaped supporting means 130, 132 and the stoppers 136. Here, the angle β corresponds to a value obtained by subtracting the angle δ from the angle α. If the V-shaped roller type hyperthermo-radiative apparatus 100 is manufactured such that the angle α is identical to the angle δ, the angle β is zero. Thus, even if the V-shaped roller type hyperthermo-radiative apparatus 100 ascends the curved portions 222, 224, the rotating members 140 can continuously remain in the horizontal state, so that the user receives relatively smaller pressure from the rotating members 140 and the friction resistance generated between the user and the rotating members 140 is relatively reduced. This is true not only when the V-shaped roller type hyperthermo-radiative apparatus 100 ascends the curved portions 222, 224 but also when it descends the curved portions. Therefore, it is preferred that the angle δ be set to be larger than zero but equal to or smaller than the angle α.

Figure 6A:
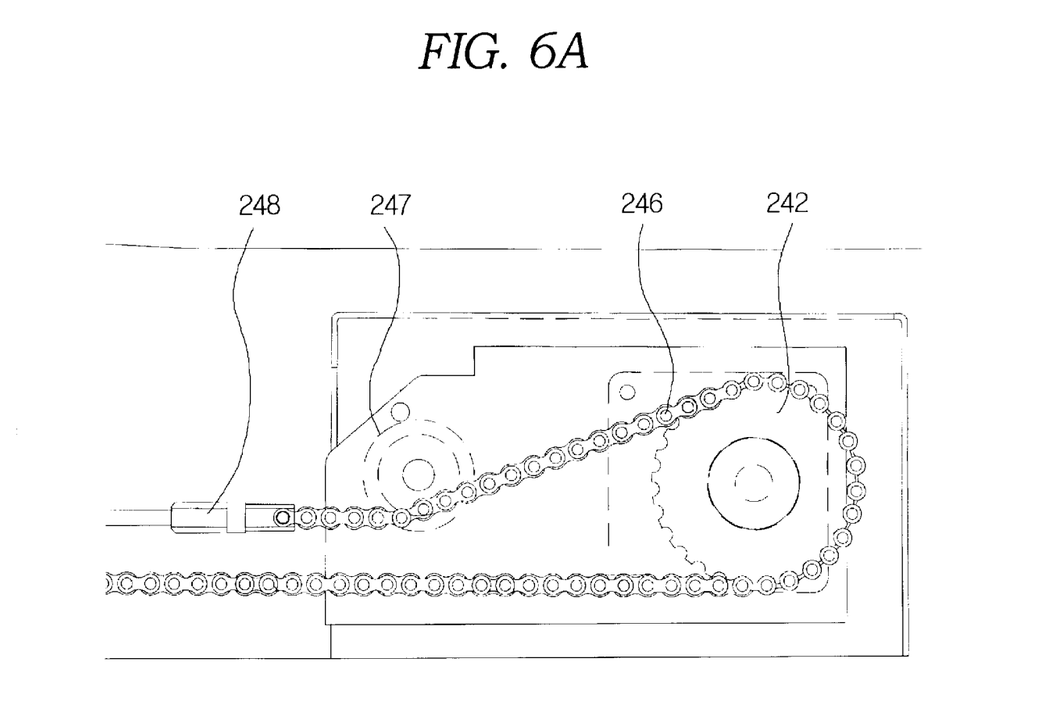
FIG. 6A illustrates the connection relationship between a power source and a conveying means.
Figure 6B:
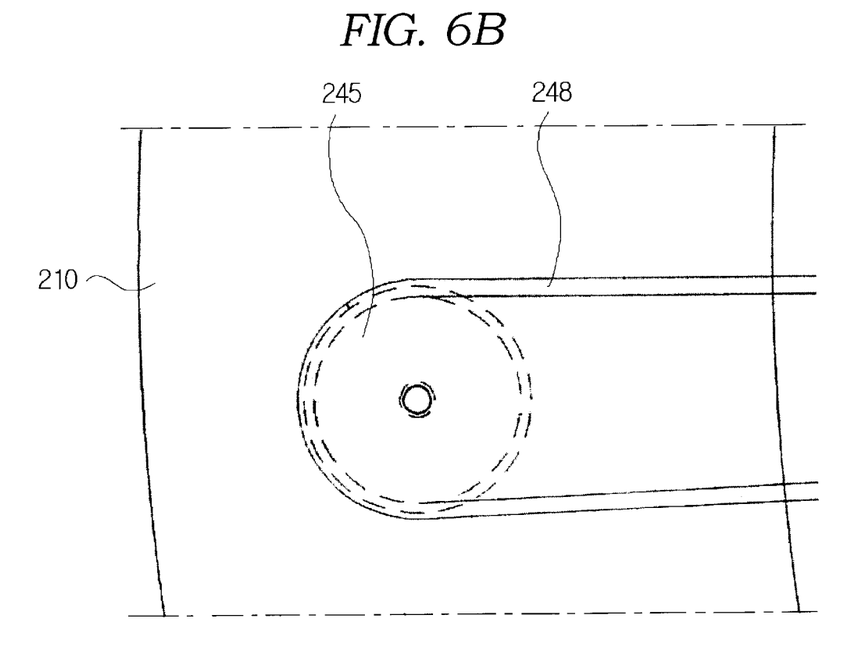
FIG. 6B shows components of the conveying means disposed on the side opposite to the power source.
Figure 6C:
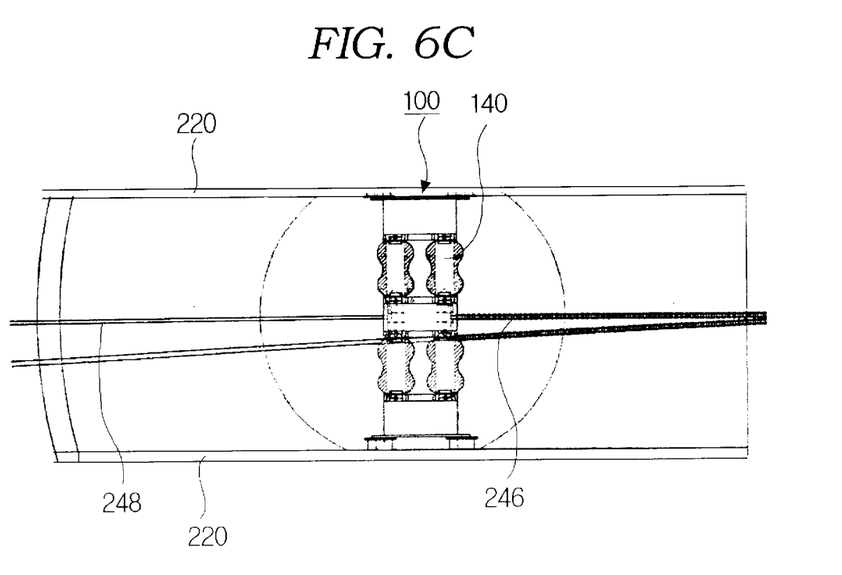
FIG. 6C illustrates the connection relationship between the conveying means and the roller type hyperthermo-radiative apparatus.

FIGS. 6A to 6C show the conveying means. The present invention includes the conveying means for moving the roller type hyperthermo-radiative apparatus 100 in the horizontal direction. Specifically, FIG. 6A shows the connection relationship between the power source and the conveying means. FIG. 6B shows components of the conveying means disposed on the side opposite to the power source. FIG. 6C shows the connection relationship between the conveying means and the roller type hyperthermo-radiative apparatus 100. The conveying means includes a gear 242 connected to a motor 240 (see FIG. 7) as the power source, and a chain 246 connected to the gear 242. The chain 246 is engaged with the gear 242 to nearly completely transmit the power generated from the motor 240 to the roller type hyperthermo-radiative apparatus 100 directly or via a wire 248. It is preferred that a height-adjusting means 247 be installed on the chain 246 so that the chain 246 can be flush with the connecting member 124 of the roller type hyperthermo-radiative apparatus 100. The chain 246 is connected directly to the connecting member 124 (see FIG. 6C), or connected thereto via the wire 248 (see FIG. 6A). On the other hand, one end of the wire 248 may be connected to the chain 246 and the other end thereof may be connected to the opposite connecting member 124 of the roller type hyperthermo-radiative apparatus 100. If two wires 248 are used, the chain 246 may be always indirectly connected to the connecting member 124 via the wires 248. The wire 248 turns around an idle pulley 245 installed on the side opposite to the motor 240 and is then connected to the opposite connecting member 124. At this time, it is preferred that the idle pulley 245 be disposed in such a manner that the wire 248 connected to the connecting member 124 of the roller type hyperthermo-radiative apparatus is parallel to the curved rails 220 (see FIG. 6C). The same is also applied to the chain 246 connected to the connecting member 124 of the roller type hyperthermo-radiative apparatus. Thus, the chain 246 and wire 248 connected to the roller type hyperthermo-radiative apparatus 100 are disposed to be parallel to the curved rails 220 as shown in FIG. 6C. Consequently, the roller type hyperthermo-radiative apparatus 100 can stably and uniformly reciprocate in the linear motion along the curved rails 220.

Figure 7:
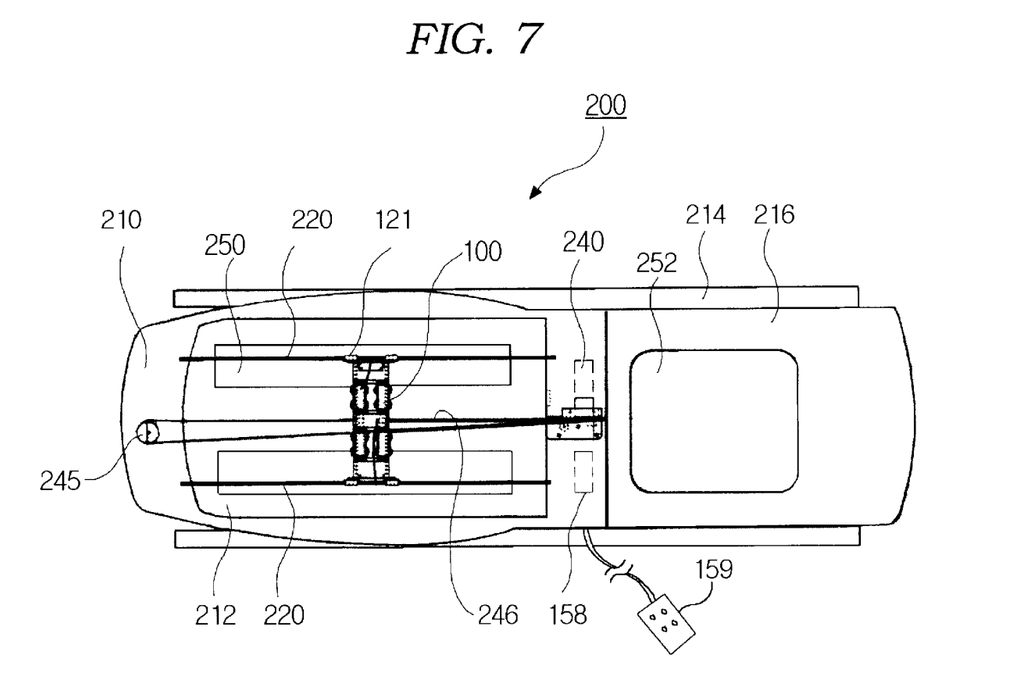
FIG. 7 shows specifically installation positions of far infrared heating means according to the present invention.

Further, in order to further enhance the effects of hot compress and far infrared radiation of the present invention, it is preferred that additional far infrared heating means 250, 252 be installed. FIG. 7 specifically shows installation positions of the additional far infrared heating means. In the present invention, it is preferred that the far infrared heating means 250, 252 be selected as a means capable of spontaneously emitting the far infrared radiation without intervention of other components when external electric energy is supplied thereto. This is because other components can be eliminated and thus the effects of the mat can be enhanced while making the mat smaller. In present invention, it is preferred that the far infrared heating means 250, 252 be products comprised of flat carbon fiber heating elements in the form of a plate. Further, the far infrared heating means 250 is preferably constructed by installing an elongated rectangular flat carbon fiber heating element parallel to and below the curved rails 220, and the other far infrared heating means 252 is constructed by installing a square flat carbon fiber heating element within the foldable mat member 216. The far infrared heating means 250 is intended to continuously emit the far infrared radiation toward the vertebral and shoulder regions of the user after the roller type hyperthermo-radiative apparatus 100 passed by the regions, whereas the other far infrared heating means 252 is intended to emit the far infrared radiation toward the leg regions of the user. In such way, when the user operates the roller type hyperthermo-radiative apparatus 100 while lying down the mat according to the present invention, the user can continuously obtain the effects of both the roller type hyperthermo-radiative apparatus and the far infrared heating means. On the other hand, since the far infrared heating means 250, 252 generally emit the far infrared radiation upon receipt of the external electric power and a means for supplying the electric power is also merely conventional, a detailed description thereof will be omitted.

The mat 200 according to the present invention includes a control panel 158 for controlling the operations of the respective components individually and as a whole, and an operating unit 159 for adjusting the position of the roller type hyperthermo-radiative apparatus 100. However, since the control panel 158 and the operating unit 159 have been generally used in such a mat, a detailed description thereof will be omitted. In addition, since the power supply (not shown) for supplying external electric power to the respective components of the present invention is also a conventional one, a detailed description thereof will be omitted.

The mat 200 of the present invention constructed as such operates as follows. After the user turns on the power source for the mat, he/she manipulates the operating unit 159 while lying down on the mat. Then, the electric power is supplied to the heating member 142 which in turn is turned on. In order to move the roller type hyperthermo-radiative apparatus 100, if necessary, the motor 240 is rotated. Accordingly, the gear 242 directly coupled with a shaft of the motor 240 is rotated and thus the chain 246 pulls the backing plate 120. As a result, the roller type hyperthermo-radiative apparatus 100 can be smoothly moved by the chain 246 and the gear 242 forward or rearward without any slippage. During such procedure, the rotating members 140 of the roller type hyperthermo-radiative apparatus 100 perform acupressure with respect to and transfer heat to the vertebral acupressure points of the user, so that the far infrared radiation penetrates into the vertebral region of the user. Further, as the roller type hyperthermo-radiative apparatus 100 advances, the rotating members 140 are smoothly rotated. This rotation imparts only rolling resistance, resulting in reduced friction resistance. Consequently, the power needed for the pulling of the roller type hyperthermo-radiative apparatus is lowered as compared with a conventional one. Thus, the present invention can employ a low-power motor, and thus, waste of the electric power can be prevented. In addition, the sizes of operating portions can be reduced, resulting in compactness of the product. Furthermore, noise can be reduced in operation.

According to the present invention, while the roller type hyperthermo-radiative apparatus moves along the curved rails, it travels in such a manner that it confronts the two curved portions, and then sequentially ascends and descends the curved portions. Since the curved portions are constructed to correspond to the upwardly raised vertebral region and the nape region of the neck of the user, such travel of the roller type hyperthermo-radiative apparatus allows the acupressure effects to be enhanced. If the user also operates the far infrared heating means, the far infrared radiation is emitted toward the whole body of the user, thereby further enhancing the radiation effects of the present invention.

During the operation, when the roller type hyperthermo-radiative apparatus reaches a position adjacent to one end of the curved rail, this is detected by a sensor (not shown) and then the motor is rotated in the reverse direction. Accordingly, the roller type hyperthermo-radiative apparatus is moved backward. Since the operating time and temperature of the roller type hyperthermo-radiative apparatus can be controlled by a conventional controller.

Although the preferred embodiments of the mat according to the present invention have been described with reference to the accompanying drawings, the present invention is not limited thereto. It is apparent that various changes and modifications may be made thereto by those skilled in the art without departing from the spirit and scope of the invention as defined by the appended claims.

What is claimed is:

1. A mat for hot compress and acupressure, comprising:
   a) a mat member foldable at one side thereof and with a longitudinal groove formed in the center thereof;

b) curved rails formed at both sides of the central groove on the bottom of the mat member and with curved portions corresponding to the curvature of the vertebral region of a user;

c) a roller type hyperthermo-radiative apparatus traveling along the curved rails;

d) a conveying means for moving the roller type hyperthermo-radiative apparatus in a horizontal direction;

e) a control panel for controlling the conveying means; and f) an operating unit for adjusting a position of the roller type hyperthermo-radiative apparatus.

2. The mat as claimed in claim 1, wherein the roller type hyperthermo-radiative apparatus includes:

a) a backing plate with wheels fixedly supported at four corners thereof;

b) a plurality of pairs of supporting means mounted on the backing plate;

c) roller type rotating members rotatably installed between respective pairs of the supporting means and with cylindrical empty spaces formed therein;

d) heating members inserted into the empty spaces of the rotating members from both ends of the spaces;

e) socket portions connected to the heating members for supplying external electric power; and f) bearing members for fixedly supporting the socket portions to the supporting mean and for rotatably coupling the rotating members thereto.

3. The mat as claimed in claim 2, wherein the roller type rotating members are comprised of an inorganic mineral containing jade as a major composition which can emit far infrared radiation upon receipt of heat.

4. The mat as claimed in claim 3, wherein each of the roller type rotating members includes outwardly protruding peak portions and a relatively indented valley portion.

5. The mat as claimed in claim 1, wherein each of the curved rails includes a curved portion and another curved portion which correspond to curvatures of the lumbar vertebral region and the nape region of the neck of the user, respectively.

6. The mat as claimed in claim 5, wherein the roller type hyperthermo-radiative apparatus includes:

a) a backing plate with wheels fixedly supported at four corners thereof;

b) a plurality of pairs of supporting means mounted on the backing plate;

c) roller type rotating members rotatably installed between respective pairs of the supporting means and with cylindrical empty spaces formed therein;

d) heating members inserted into the empty spaces of the rotating members from both ends of the spaces;

e) socket portions connected to the heating members for supplying external electric power; and f) bearing members for fixedly supporting the socket portions to the supporting means and for rotatably coupling the rotating members thereto.

7. The mat as claimed in claim 6, wherein the roller type rotating members are comprised of an inorganic mineral containing jade as a major composition which can emit far infrared radiation upon receipt of heat.

8. The mat as claimed in claim 7, wherein each of the roller type rotating members includes outwardly protruding peak portions and a relatively indented valley portion.

9. The mat as claimed in claim 1, wherein the conveying means includes a gear connected to a motor as a power source, a chain engaged with the gear, and wire with one end thereof connected to the chain and with the other end thereof connected to the roller type hyperthermo-radiative apparatus; and the wire turns around an idle pulley installed on the side opposite to the motor and is then connected to an opposite connecting member of the roller type hyperthermo-radiative apparatus.

10. The mat as claimed in claim 9, wherein a height-adjusting means is installed on the chain so that the chain can be flush with the connecting member of the roller type hyperthermo-radiative apparatus, and the idle pulley is disposed in such a manner that the wire connected to the connecting member of the roller type hyperthermo-radiative apparatus is parallel to the curved rails.

11. The mat as claimed in claim 10, wherein the roller type hyperthermo-radiative apparatus includes:

a) a backing plate with wheels fixedly supported at four corners thereof;

b) a plurality of pairs of supporting means mounted on the backing plate;

c) roller type rotating members rotatably installed between respective pairs of the supporting means and with cylindrical empty spaces formed therein;

d) heating members inserted into the empty spaces of the rotating members from both ends of the spaces;

e) socket portions connected to the heating members for supplying external electric power; and f) bearing members for fixedly supporting the socket portions to the supporting means and for rotatably coupling the rotating members thereto.

12. The mat as claimed in claim 11, wherein the roller type rotating members are comprised of an inorganic mineral containing jade as a major composition which can emit far infrared radiation upon receipt of heat.

13. The mat as claimed in claim 12, wherein each of the roller type rotating members includes outwardly protruding peak portions and a relatively indented valley portion.

14. The mat as claimed in claim 1, wherein the mat member further includes a mat member electrically connected to and foldable toward the mat member.

15. The mat as claimed in claim 14, further comprising far infrared heating means installed in the groove of the mat member and within the mat member, respectively.

16. The mat as claimed in claim 15, wherein the far infrared heating means are products comprised of flat carbon fiber heating elements.

17. The mat as claimed in claim 16, wherein the roller type hyperthermo-radiative apparatus includes:

a) a backing plate with wheels fixedly supported at four corners thereof;

b) a plurality of pairs of supporting means mounted on the backing plate;

c) roller type rotating members rotatably installed between respective pairs of the supporting means and with cylindrical empty spaces formed therein;

d) heating members inserted into the empty spaces of the rotating members from both ends of the spaces;

e) socket portions connected to the heating members for supplying external electric power; and f) bearing members for fixedly supporting the socket portions to the supporting means and for rotatably coupling the rotating members thereto.

18. The mat as claimed in claim 17, wherein the roller type rotating members are comprised of an inorganic mineral containing jade as a major composition which can emit far infrared radiation upon receipt of heat.

19. The mat as claimed in claim 18, wherein each of the roller type rotating members includes outwardly protruding peak portions and a relatively indented valley portion.

20. The mat as claimed in claim 19, wherein each of the curved rails includes a curved portion and another curved portion which correspond to curvatures of the lumbar vertebral region and the nape region of the neck of the user, respectively.

21. The mat as claimed in claim 20, wherein the conveying means includes a gear connected to a motor as a power source, a chain engaged with the gear, and wire with one end thereof connected to the chain and with the other end thereof connected to the roller type hyperthermo-radiative apparatus; and the wire turns around an idle pulley installed on the side opposite to the motor and is then connected to an opposite connecting member of the roller type hyperthermo-radiative apparatus.

22. The mat as claimed in claim 21, wherein a height-adjusting means is installed on the chain so that the chain can be flush with the connecting member of the roller type hyperthermo-radiative apparatus; and the idle pulley is disposed in such a manner that the wire connected to the connecting member of the roller type hyperthermo-radiative apparatus is parallel to the curved rails.

* * * * *